United States Patent
Bergmann et al.

(10) Patent No.: US 8,465,941 B2
(45) Date of Patent: Jun. 18, 2013

(54) PROCALCITONIN-BASED DIAGNOSIS OF INFECTIONS OR INFLAMMATORY DISEASES OF THE RESPIRATORY TRACT IN A PATIENT WITH HEART FAILURE

(75) Inventors: Andreas Bergmann, Berlin (DE); Nils Morgenthaler, Berlin (DE); Jana Papassotiriou, Berlin (DE); Joachim Struck, Berlin (DE)

(73) Assignee: B.R.A.H.M.S. GmbH, Henningsdorf (DE)

( * ) Notice: Subject to any disclaimer, the term of this patent is extended or adjusted under 35 U.S.C. 154(b) by 294 days.

(21) Appl. No.: 12/443,897

(22) PCT Filed: Oct. 1, 2007

(86) PCT No.: PCT/DE2007/001759
§ 371 (c)(1), (2), (4) Date: Jun. 25, 2009

(87) PCT Pub. No.: WO2008/040328
PCT Pub. Date: Apr. 10, 2008

(65) Prior Publication Data
US 2010/0047835 A1 Feb. 25, 2010

(30) Foreign Application Priority Data
Oct. 1, 2006 (DE) .......................... 10 2006 046 996

(51) Int. Cl.
*C12Q 1/48* (2006.01)
(52) U.S. Cl.
USPC .......................................................... 435/15

(58) Field of Classification Search
USPC ............................................. 435/15; 436/86
See application file for complete search history.

(56) References Cited

U.S. PATENT DOCUMENTS

| | | | |
|---|---|---|---|
| 6,562,946 B2 | 5/2003 | Althaus et al. | |
| 6,756,483 B1 | 6/2004 | Bergmann et al. | |
| 6,905,687 B2 | 6/2005 | Althaus et al. | |
| 7,338,770 B2 | 3/2008 | Althaus et al. | |
| 2004/0121343 A1* | 6/2004 | Buechler et al. | 435/6 |
| 2010/0041064 A1* | 2/2010 | Bergmann et al. | 435/7.1 |
| 2011/0039283 A1* | 2/2011 | Bermann et al. | 435/7.94 |

FOREIGN PATENT DOCUMENTS

| | | |
|---|---|---|
| DE | 10027954 A1 | 6/2001 |
| EP | 0656121 B1 | 3/1998 |
| EP | 1121600 B1 | 3/2006 |

OTHER PUBLICATIONS

Sandek A. et al. Procalcitonin Guided Antibiotic Treatment in Heart Failure. The Lancet 363(9420)1555-6, May 8, 2004.*
Sandek A. et al. Procalcitonin Guided Antibiotic Treatment in Heart Failure. The Lancet 363(9420)1555, May 8, 2004.*
Christ-Crain M. et al. Effect of Procalcitonin Guided Treatment on Antibiotic Use . . . The Lancet 363(9409)600-607, Feb. 22, 2004.*

(Continued)

*Primary Examiner* — Ralph Gitomer
(74) *Attorney, Agent, or Firm* — Millen, White, Zelano & Branigan, P.C.

(57) ABSTRACT

The invention relates to a method for diagnosis of infections or inflammatory diseases of the airways and lungs with associated heart failure, wherein the marker procalcitonin or a partial sequence thereof is determined in a patient to be examined, in particular for classifying patients according to risk. The invention further relates to a diagnostic device and kit for carrying out the method.

18 Claims, 6 Drawing Sheets

Figure 1:
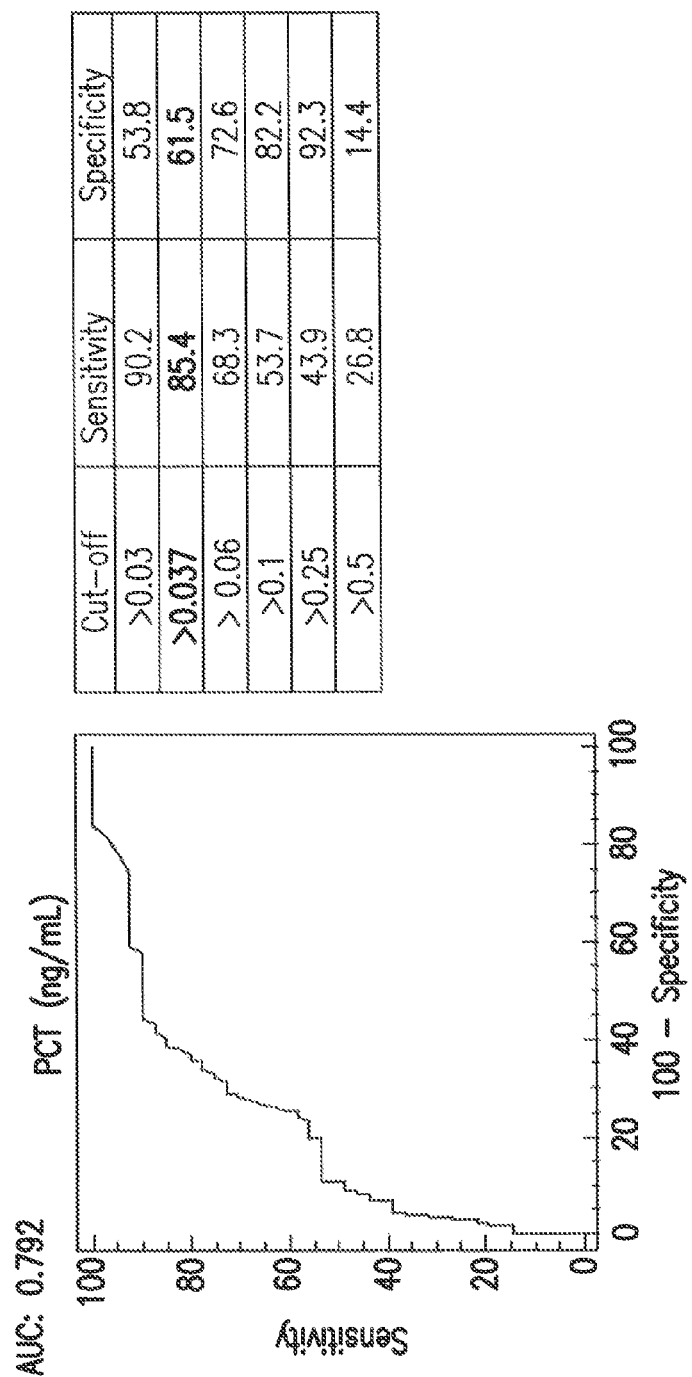

| Cut-off | Sensitivity | Specificity |
|---|---|---|
| >0.03 | 90.2 | 53.8 |
| >0.037 | 85.4 | 61.5 |
| >0.06 | 68.3 | 72.6 |
| >0.1 | 53.7 | 82.2 |
| >0.25 | 43.9 | 92.3 |
| >0.5 | 26.8 | 14.4 |

OTHER PUBLICATIONS

Remskar M. et al. Procalcitonin in Patients with Acute Myocardial Infarction. Wiener Klinische Wochenschrift 114(5-6)205-210 2002.*

Ferriere F. Procalcitonin: A New Marker for Bacterial Infections. Annales de Biologie Clinique 58(1)49-59, 2000.*

Maisel Statement in corresponding EPO prosecution; Dec. 5, 2012, 4 pages.

Christ-Crain, M., et al., "Procalcitonin Guidance of Antibiotic Therapy in Community-acquired Pneumonia—A Randomized Trial," American Journal of Respiratory and Critical Care Medicine, vol. 174, 2006, pp. 84-93.

* cited by examiner

PROCALCITONIN-BASED DIAGNOSIS OF INFECTIONS OR INFLAMMATORY DISEASES OF THE RESPIRATORY TRACT IN A PATIENT WITH HEART FAILURE

RELATED APPLICATIONS

This application is a national stage application (under 35 U.S.C. §371) of PCT/DE2007/001759, filed Oct. 1, 2007, which claims benefit of German application 102006046996.8, filed Oct. 1, 2006.

The invention relates to a method for the diagnosis of infections or inflammatory diseases of the airways and lungs with associated heart failure, where a determination of the marker procalcitonin or a partial sequence thereof is carried out in a patient to be examined, particularly for the purpose of classifying patients according to risk. Furthermore, the invention relates to a diagnostic device and a kit for carrying out the method.

In Europe, about a million patients a year come to the emergency admission departments of clinics with the symptom of acute respiratory distress. Respiratory distress is a leading symptom of many diseases, and can be attributed to heart failure in approximately 35-47% of the cases (Januzzi J L Jr, Camargo C A, Anwaruddin S, Baggish A L, Chen A A, Krauser D G, Tung R. Cameron R, Nagurney J T, Chae C U, Lloyd-Jones D M, Brown D F, Foran-Melanson S, Sluss P M, Lee-Lewandrowski E, Lewandrowski K B, The N-terminal Pro-BNP investigation of dyspnea in the emergency department (PRIDE) study, Am J Cardiol. 95(8) (2005), pp. 948-954 and Maisel A S, Krishnaswamy P, Nowak R M, McCord J, Hollander J E, Duc P, Omland T, Storrow A B, Abraham W T, Wu A H, Clopton P, Steg P G, Westheim A, Knudsen C W, Perez A, Kazanegra R, Herrmann H C, McCullough P A; Breathing Not Properly Multinational Study Investigators, Rapid measurement of B-type natriuretic peptide in the emergency diagnosis of heart failure, N Engl J Med. 347(3) (2002), pp. 161-167) and to pneumonia in approximately 11% of the cases (Januzzi J L et al, 2005 (supra)). Since heart failure is a decisive risk factor for the occurrence of pneumonias (Huntemann I, Lorenz J, Ambulant erworbene Pneumonie {Pneumonia acquired as an out-patient} (AEP), overview article on the CAPNETZ web site: www.capnetz.de), the two diseases can be associated with one another, and some of the patients who come to the emergency room suffer both from pneumonia and from heart failure (Christ-Crain M, Stolz D, Bingisser R, Muller C, Miedinger D, Huber P R, Zimmerli W, Harbarth S, Tamm M, Muller B, Procalcitonin Guidance of Antibiotic Therapy in Community-acquired Pneumonia: A Randomized Trial, Am J Respir Crit Care Med 174(1) (2006), pp. 84-93). In order to begin suitable therapy, an early diagnosis and differentiation of the underlying disease/diseases that already takes place in the emergency room is required. Because of the non-specific symptoms (difficulty breathing, coughing) of the two diseases (heart failure and pneumonia), both differentiation and a distinction between the two illnesses, and the recognition that they are occurring simultaneously, is frequently difficult (Huntemann I et al. (supra) and Maisel A S et al, 2002 (supra)). In order to facilitate the diagnosis, laboratory studies that are carried out are the determination of the B-type natriuretic peptide (BNP), i.e. its hormone fragments such as NT-proBNP (Januzzi J L et al, 2005 (supra) and Maisel A S et al, 2002 (supra)) and of the C-reactive protein. A low BNP value of <100 pg/ml can lead to exclusion of the diagnosis of heart failure (Maisel A S et al, 2002 (supra) and Ray P, Lefort Y, Usefulness of B-type natriuretic peptide in emergency medicine, Rev Med Interne 27 (2006), Epub ahead of print); a very high value >500 pg/ml makes the presence of heart failure likely (Ray P et al. (2006) (supra)). The assessment of the CRP for confirmation or exclusion of pneumonia is more difficult. On the one hand, it can be non-specifically elevated in a number of diseases not caused by pathogens (autoimmune diseases, tissue necroses, cardiac infarction) (Wicher J, C-reaktives Protein (CRP) in Labor und Diagnose, Indikation und Bewertung von Laborbefunden für die medizinische Diagnostik {C-reactive protein (CRP) in laboratory work and diagnosis, indication and assessment of laboratory findings for medical diagnoses}, published by Lothar Thomas 1998, 5$^{th}$ edition, TH-Books Verlagsgesellschaft 1998). On the other hand, the heart failure itself can cause an elevation in the CRP (Kardys I, Knetsch A M, Bleumink G S, Deckers J W, Hofman A, Stricker B H, Witteman J C, C-reactive protein and risk of heart failure. The Rotterdam Study, Am Heart J. 152(3) (2006): pp. 514-520). For these reasons, it is difficult to determine the concomitant presence of pneumonia in patients with heart failure, even using the usual laboratory studies. However, this is of great importance, since, as was already mentioned above, the presence of heart failure promotes pneumonia, and an early diagnosis and the resultant early treatment of pneumonia with antibiotics significantly improves the patients' prognosis (Welte T, Community-acquired and nosocomial pleumonia {sic—should be pneumonia}, Internist (Berl) 44 (2003), pp 44-58) and leads to a reduction in treatment costs.

In the state of the art, the procalcitonin (PCT) determination is described for the purpose of a study to distinguish bacterial sepsis (threshold value >0.5 ng/mL) from other disease causes (EP0656121). PCT is also described in the literature in connection with pneumonias, where the studies are primarily related, with regard to a diagnosis, to discriminating between different pathogen types in the case of pneumonia that has already been diagnosed (Prat C, Dominguez J, Andreo F, Blanco S, Pallares A, Cuchillo F, Ramil C, Ruiz-Manzano J, Ausina V, Procalcitonin and neopterin correlation with aetiology and severity of pneumonia, J Infect. 52(3) (2006): pp 169-177 and Masia M, Gutierrez F, Shum C, Padilla S, Navarro J C, Flores B, Hernandez I, Masia M, Gutierrez F, Shum C, Padilla S, Navarro J C, Flores E, Hernandez I {sic—repetition of names in original}, Chest 128(4) (2005): pp 2223-2239, Boussekey N, Leroy O, Georges H, Devos P, d'Escrivan T, Guery B, Diagnostic and prognostic values of admission procalcitonin levels in community-acquired pneumonia in an intensive care unit. Infection 33(4) (2005): pp 257-63). In a study by Zhou et al (Zhou C D et al Zhonguo Wei Zhong Bing Ji Jiu Yi Xue. 2006 June, 18(6), 370-2), PCT is presented as a diagnostic marker for early diagnosis of ventilator-associated pneumonia in an intensive care unit. PCT is also described as a diagnostic marker in pneumonias (Prat et al. 2006 (supra) and Masia M et al. 2005 (supra), Boussekey N et al. 2005 (supra), Christ-Crain M, Morgenthaler N G, Solz D, Muller C, Bingisser R, Harbarth S, Tamm M, Struck J, Bergmann A, Muller B, Pro-adrenomedullin to predict severity and outcome in community-acquired pneumonia, Crit Care 10(3) (2006): pp R96). Furthermore, there are studies in which it was shown that clinically relevant infections (including bacterial pneumonias) that require antibiotic therapy are detected in patients who are suspected of having infections of the lower airways (including pneumonia), using PCT, at a threshold concentration of >0.1 ng/mL and >0.25 ng/mL, respectively (Christ-Cran M, Stolz D, Bingisser R, Muller C, Miedinger D, Huber P R, Zimmerli W, Harbarth S, Tamm M, Muller B, Procalcitonin Guidance of Antibiotic Therapy in Community-acquired Pneumonia: A Randomized Trial, Am J Respir Crit Care Med 174(1) (2006), pp. 84-93 and Christ-Crain M, Jaccard-Stolz D, Bingisser R, Gencay M M, Huber P R, Tamm M, Muller B, Effect of procalcitonin-guided treatment on antibiotic use and outcome in lower respiratory tract infections: cluster-randomized, single-blinded intervention trial, Lancet 21; 363 (9409) (2004): pp 600-607, Stolz D, Christ-Crain M, Gencay M M, Bingisser R, Huber P R, Muller B, Tamm M, Diagnostic value of signs, symptoms and laboratory values in lower respiratory tract infection, Swiss Med Wkly 8; 136(27-28) (2006): pp 434-440).

However, no method is known for the diagnosis of infections or inflammatory diseases of the airways and lungs with associated heart failure.

It is therefore the task of the present invention to make available a method for the diagnosis of infections or inflammatory diseases of the airways and lungs with associated heart failure.

This task is accomplished by means of a method for the diagnosis of infections or inflammatory diseases of the airways and lungs with associated heart failure, where a determination of the marker procalcitonin (PCT) or a partial sequence thereof is carried out in a patient to be examined thereinafter: method according to the invention).

In a preferred embodiment of the method according to the invention, the significant range is 0.01 ng/mL to 1 ng/mL of procalcitonin (PCT) determined, with a threshold value of 0.03 ng/mL to 0.06 ng/mL PCT (ROC curves, see examples and figures).

The term "infections or inflammatory diseases of the airways and lungs with associated heart failure" particularly comprises the comorbidity of these indications, i.e. in addition to an existing underlying disease (index disease), namely heart failure, an existing, diagnostically distinguishable disease profile, namely infection or inflammatory diseases, is determined, i.e. there is an associated disease profile that can lead to an incorrect diagnosis or incorrect interpretation, particularly due to similarity of symptoms (difficulty breathing, chest pains), since the one disease profile overlaps the other disease profile.

A reliable diagnosis can take place by means of the method according to the invention, in particularly advantageous manner, and especially in cases of emergency and/or intensive care medicine. The method according to the invention allows clinical decisions that lead to rapid therapy success. Such clinical decisions also comprise further therapy by means of medications for treatment or therapy of heart failure, and for treatment or therapy of infections/inflammatory diseases of the airways and lungs.

In another preferred embodiment, the method according to the invention therefore relates to therapy control for antibiotic treatment of an infection/inflammatory disease of the airways and lungs.

For this reason, the invention also relates to a method for classifying the risk of patients, particularly for classifying the risk of patients for clinical decisions, preferably in intensive care medicine or emergency medicine, where time is critical.

In another preferred embodiment of the method according to the invention, the diagnosis takes place for prophylaxis, for early recognition and recognition by means of a differential diagnosis, for an assessment of the degree of severity, and for an assessment of the progression of an infection or inflammatory disease of the airways and lungs with associated heart failure, over the course of therapy.

In another embodiment of the method according to the invention, blood is taken from the patient to be examined, optionally whole blood or serum, and the diagnosis takes pace in vitro/ex vivo, i.e. outside of the human or animal body. The diagnosis can take place on the basis of the determination of the marker procalcitonin and the amount thereof that is present in at least one patient sample.

Within the scope of this invention, the term "heart failure" is {words missing: understood to mean} acute or chronic inability of the heart to supply the tissues with sufficient blood, and, as a result of this, with sufficient oxygen, in order to ensure tissue metabolism at rest or under stress. Clinically, heart failure is present if typical symptoms (dyspnea, tiredness, fluid retention) are present, which are caused by cardiac dysfunction in the sense of systolic or diastolic dysfunction. Chronic heart failure (CHF) is also included, according to the invention (Kardiologie {Cardiology} compact, published by Christian Mewis, Reimer Riessen, and loakim Spyridopoulos, $2^{nd}$ unchanged edition, Thieme 2006).

Within the scope of this invention, "infections of the lungs and airways" are understood to mean, in particular, those infections that are caused by bacteria, viruses, fungi, or parasites, e.g. indications such as bronchitis, pneumonia, sarcoidosis, bronchiectases, non-cardiac pulmonary edema. Furthermore, bronchitis, putrid bronchitis, pneumonia are preferred according to the invention. Pneumonia is very particularly preferred.

Within the scope of this invention, pneumonia (inflammation of the lungs) is understood to be an acute or chronic inflammation of the lung tissue, and the infection is caused by bacteria, viruses, or fungi, rarely also toxically, due to inhalation of toxic substances, or immunologically. For a clinician, pneumonia is a constellation of various symptoms (fever or hypothermia, shivering, coughing, pleuritic thorax pain, increased sputum production, increased respiratory rate, auscultation damping, bronchial breathing, crepitation close to the ear, pleura rubbing) in combination with at least one infiltrate that can be seen on the thorax X-ray (Harrisons Innere Medizin {Harrison's Internal Medicine}, published by Manfred Dietel, Norbert Suttorp, and Martin Zeitz, ABW Wissenschaftsverlag 2005).

Within the scope of this invention, "inflammation diseases of the lungs and airways" or "inflammatory diseases of the lungs and airways" are understood to be those indications such as interstitial lung diseases and lung fibroses, chronic obstructive pulmonary diseases (COPD), particularly COPD infection exacerbations, bronchial asthma, particularly infection exacerbations in cases of bronchial asthma, bronchial carcinoma.

All the indications mentioned are furthermore described in Pschyrembel, De Gruyter, Berlin 2004, for example.

Within the scope of this invention, "procalcitonin" is understood to be a human protein or polypeptide having an amino acid sequence of amino acids 1-116, or amino acids 2-116 (PCT 2-116) or amino acids 3-116 (PCT 3-116), as described in EP0656121, EP1121600 of the applicant, as well as DE10027954A1. Furthermore, the procalcitonin according to the invention can demonstrate post-translational modifications, such as glycolization, lip(o)idization, or derivativization. Furthermore, partial sequences or fragments of procalcitonin are also included.

In another embodiment, the determination of procalcitonin can additionally take place with further markers, specifically preferably those that already indicate heart failure or infection/inflammatory diseases of the airways and lungs.

For this reason, the invention relates to an embodiment of the method according to the invention where the determination is additionally carried out with at least one further marker selected from the group of inflammatory markers, cardiovascular markers, neurohormonal markers, or ischemic markers, in a patient to be examined.

According to the invention, the inflammatory marker can be selected from at least one marker of the group of C-reactive protein (CRP), cytokines, such as TNF-alpha, for example, interleukins, such as IL-6, for example, and adhesion molecules, such as VCAM or ICAM, GDF-15 or ST2, and the cardiovascular marker can be selected from at least one marker of the group of creatine kinase, myoglobin, natriuretic protein, particularly ANP (or ANF), proANP, NT-proANP, BNP, proBNP, NT-proBNP, or a partial sequence thereof, in each instance, cardiac troponin, CRP. Furthermore, this term is also understood to mean circulation-regulating (pro)hormones, particularly such as pro-gastrin-releasing peptide (proGRP), pro-endothelin-1, pro-leptin, pro-neuropeptide-Y, pro-somatostatin, pro-neuropeptide-YY, pro-opiomelanocortin, or pro-adrenomedullin (proADM), or a partial sequence thereof, in each instance.

The ischemic marker can be selected from at least one marker from the group of troponin I and T, CD-MB. Furthermore, the neurohormonal marker can be at least one natriuretic protein, particularly ANP (or ANF), proANP, NT-proANP, BNP, proBNP, NT-proBNP, or a partial sequence thereof, in each instance.

In another embodiment of the invention, the method according to the invention can be carried out by means of parallel or simultaneous determination of the markers (e.g. multi-titer plates with 96 cavities and more), where the determinations are carried out on at least one patient sample.

Furthermore, the method according to the invention and its determinations can be carried out using an automated analysis device, particularly using a Kryptor (http://www.kryptor.net/).

In another embodiment, the method according to the invention and its determinations can be carried out by means of a rapid test (e.g. lateral flow test), whether using single-parameter or multi-parameter determinations.

Furthermore, the invention relates to the use of procalcitonin or a partial sequence thereof, and possibly additional markers, as explained above, for the diagnosis of infections or inflammatory diseases of the airways and lungs with associated heart failure.

Another task is making available a corresponding diagnostic device for carrying out the method according to the invention, or its use for carrying out the method according to the invention.

Within the scope of this invention, a diagnostic device is particularly understood to be an array or assay (e.g. immune assay, ELISA, etc.), in the broadest sense a device for carrying out the method according to the invention.

The invention furthermore relates to a kit for the diagnosis or risk classification of infections or inflammatory diseases of the airways and lungs with associated heart failure, containing detection reagents for determining the marker procalcitonin or a partial sequence thereof, and possibly additional markers mentioned above. Such detection reagents comprise antibodies, immune fluorescence, etc., for example.

The following examples and figures serve for a more detailed explanation of the invention, but without restricting the invention to these examples and figures.

EXAMPLES AND FIGURES

Example 1

Blood samples were taken of patients who came to the emergency room of a hospital with the leading symptom of respiratory distress, during the initial examination. EDTA plasma obtained by means of centrifugation was aliquoted and stored at −80° C. until measurement of the PCT took place. PCT was measured using the assay B•R•A•H•M•S PCT sensitive LIA (BRAHMS AG, Hennigsdorf, Germany) (Morgenthaler N G, Struck J, Fischer-Schulz C, Bergmann A, Sensitive Immunoluminometric Assay for the Detection of Procalcitonin, Clin Chem 48 (2002), pp. 788-790). The assay has an analytical assay sensitivity of 0.01 ng/mL.

The diagnosis of heart failure in the patients examined was based on the Framingham Score (McKee P A, Castelli W P, McNamara P, and Kannel W E, The natural history of congestive heart failure: the Framingham study, N Engl J Med 285 (1971), pp. 1441-1446) for heart failure plus echiographic evidence of systolic or diastolic dysfunction).

Pneumonia was diagnosed if a previously unknown infiltrate was observed on the X-ray, and at least two respiratory symptoms (coughing, dyspnea, or putrid ejection) had occurred.

Furthermore, blood samples were taken from healthy individuals who did not have any known disease, and EDTA plasma was obtained by means of centrifugation. The samples were stored at −20° C. until the PCT measurement (B•R•A•H•M•S PCT sensitive LIA (BRAHMS AG, Hennigsdorf, Germany)).

FIGURES AND TABLES CAPTIONS

FIG. 1:
Left: ROC curve for the diagnosis of pneumonia by means of PCT in patients who had respiratory distress when admitted to the emergency room. Patients without pneumonia: n=208; patients with the sole diagnosis of pneumonia: n=21; patients with the diagnosis of pneumonia and heart failure: n=20. The area under the curve is 0.792 (95% CI 0.736-0.840; p=0.0001).

Right: Sensitivity and specificity for the diagnosis of pneumonia by means of PCT at different threshold concentrations (cut-off [ng/mL]). Greatest diagnostic accuracy at emphasized threshold.

Figure 2:
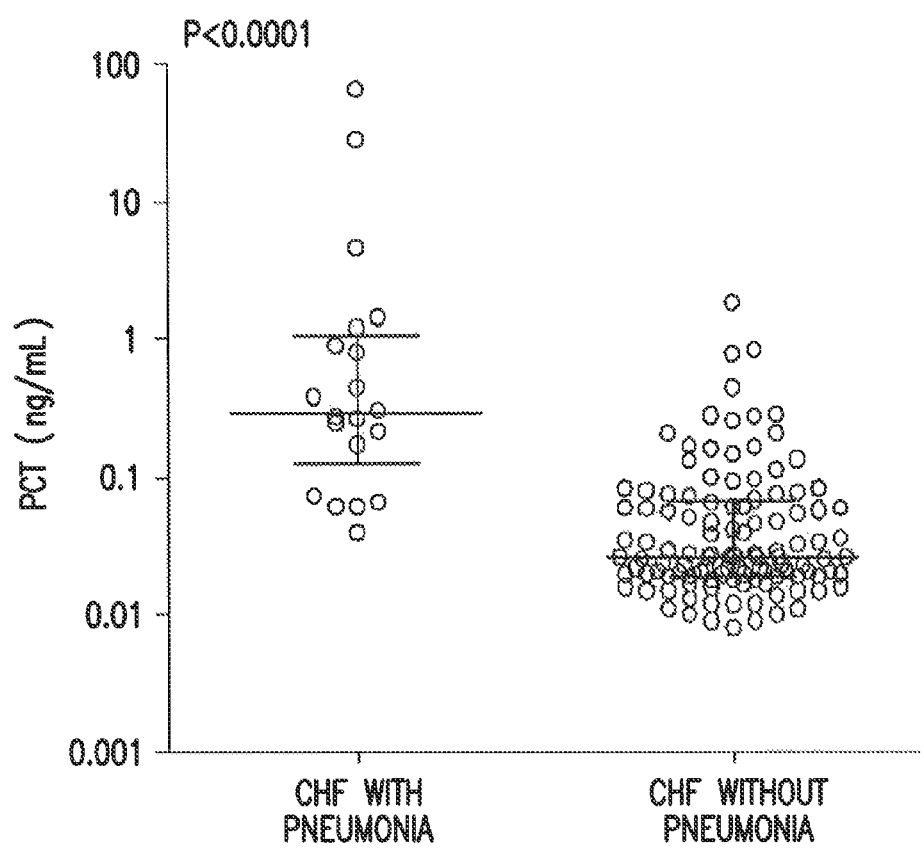

FIG. 2:
Distribution of the PCT measurement values in respiratory distress patients with heart failure (CHF). Comparison of patients with and without comorbidity pneumonia, Individual values are shown, with median and inter-quartile range. Mann-Whitney U Test: significant (P<0.0001) difference between the two groups.

Figure 3:
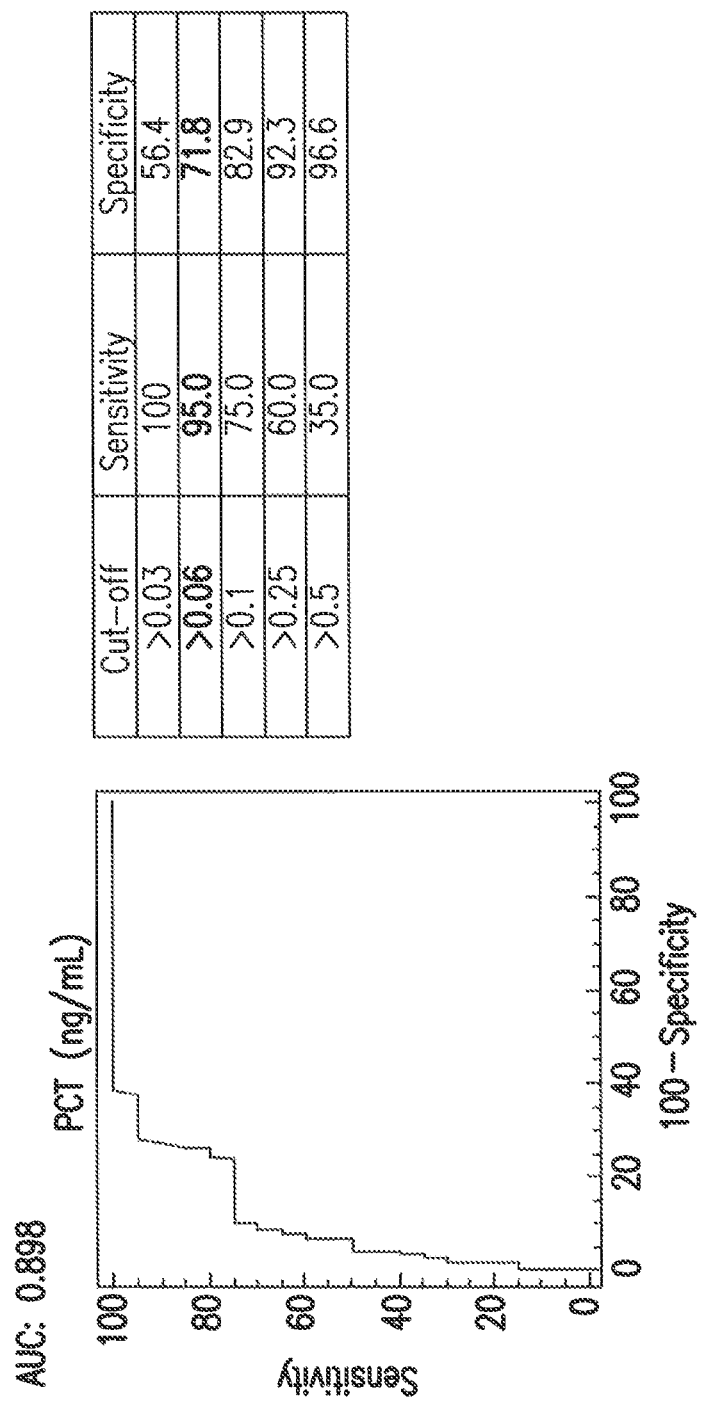

FIG. 3:
Left: ROC curve for the diagnosis of pneumonia by means of PCT in patients who had heart failure when admitted to the emergency room. Heart failure patients without pneumonia: n=117; patients with the diagnosis of pneumonia and heart failure: n=20. The area under the curve is 0.898 (95% CI 0.835-0.945; p=0.0001).

Right: Sensitivity and specificity for the diagnosis of pneumonia by means of PCT at different threshold concentrations (cut-off [ng/mL]). Greatest diagnostic accuracy at emphasized threshold.

Figure 4:
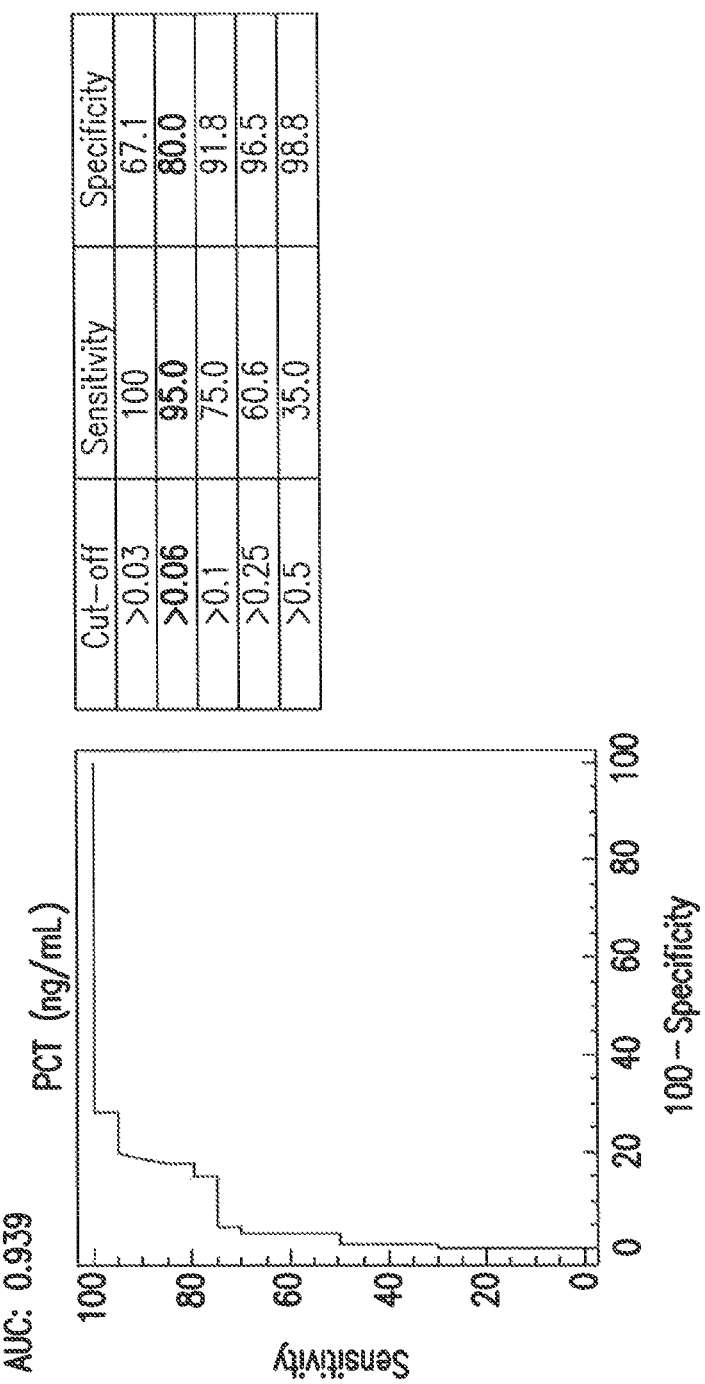
Figure 5:
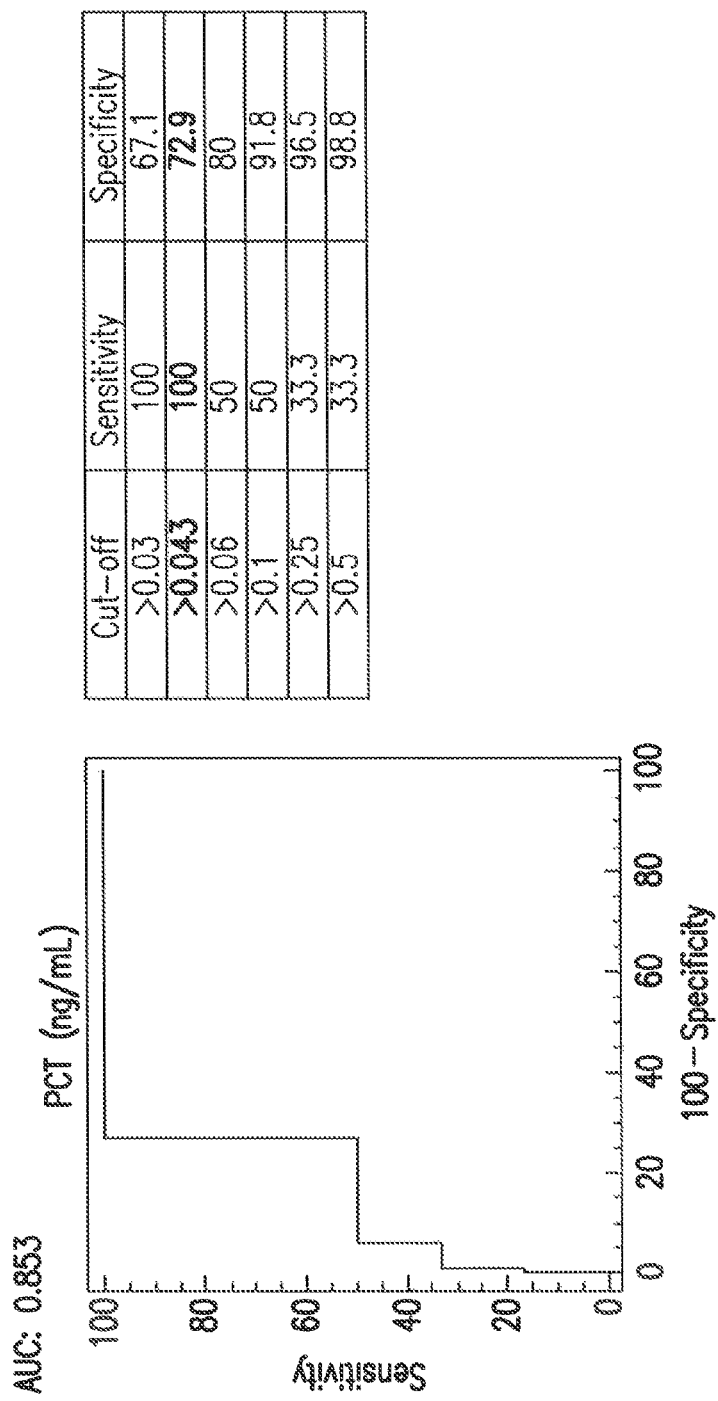
Figure 6:
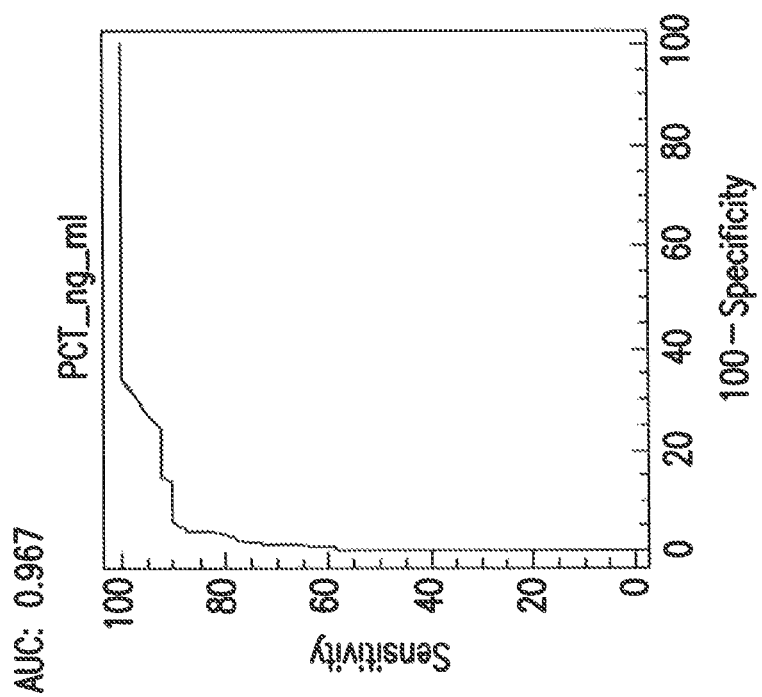

FIG. 4:
Left: ROC curve for the diagnosis of pneumonia by means of PCT in patients who had heart failure when admitted to the emergency room. In comparison with FIG. 3, the study relates only to heart failure patients without comorbidity, and those with pneumonia; heart failure patients without comorbidity: n=85; patients with the diagnosis of pneumonia and heart failure: n=20. The area under the curve is 0.939 (95% CI 0.874-0.976; p=0.0001).

Right: Sensitivity and specificity for the diagnosis of pneumonia by means of PCT at different threshold concentrations (cut-off [ng/mL]). Greatest diagnostic accuracy at emphasized threshold.

FIG. 5:

Left: ROC curve for the diagnosis of putrid bronchitis by means of PCT in patients who had heart failure when admitted to the emergency room. Heart failure patients without comorbidity: n=85; patients with the diagnosis of putrid bronchitis: n=6. The area under the curve is 0.853 (95% CI 0.763-0.918; p=0.0004).

Right: Sensitivity and specificity for the diagnosis of putrid bronchitis by means of PCT at different threshold concentrations (cut-off [ng/mL]). Greatest diagnostic accuracy at emphasized threshold.

FIG. 6:

Left: ROC curve for the diagnosis of pneumonia by means of PCT. The ROC analysis relates to a comparison of healthy test subjects and patients who came to the emergency room with the symptom of respiratory distress, and for whom pneumonia was diagnosed. Heart failure patients with diagnosis of pneumonia: n=41; healthy control individuals: n=206. The area under the curve is 0.967 (95% CI 0.940-0.984; p=0.0001).

Right: Sensitivity and specificity for the diagnosis of pneumonia by means of PCT at different threshold concentrations (cut-off [ng/mL]). Greatest diagnostic accuracy at emphasized threshold.

The invention claimed is:

1. An in vitro method for diagnosis of an infection or inflammatory disease of the respiratory tract, in a patient having cardiac insufficiency, comprising: determining the level of the biomarker procalcitonin or fragments thereof, in a sample obtained from said patient, and employing a threshold value which is used to indicate when said patient has an infection or inflammatory disease of the respiratory tract with associated cardiac insufficiency, said threshold value being a level of procalcitonin or fragments thereof that is between 0.03 ng/mL and 0.25 ng/mL.

2. The in vitro method according to claim 1, wherein the threshold value is between 0.03 ng/mL and 0.1 ng/mL.

3. The in vitro method according to claim 1, wherein the threshold value is between 0.03 ng/mL and 0.06 ng/mL.

4. The in vitro method according to claim 1, wherein the biomarker procalcitonin consists of amino acids 1-116 and/or amino acids 3-116 of procalcitonin.

5. The in vitro method according to claim 1, wherein the inflammatory disease of the respiratory tract or lung is selected from the group consisting of interstitial pulmonary diseases, lung fibrosis, chronic obstructive pulmonary disease (COPD), asthma bronchiale, and bronchial carcinoma.

6. The in vitro method according to claim 1, further comprising determining the level of one or more biomarkers selected from the group consisting of inflammatory markers, cardiovascular markers, neurohormonal markers and ischemic markers in a sample of said patient.

7. The in vitro method according to claim 6, wherein the inflammatory biomarker is one or more biomarkers selected from the group consisting of c-reactive proteins (CRP), cytokines, interleukins, and adhesion molecules.

8. The in vitro method according to claim 6, wherein the cardiovascular biomarker is one or more biomarkers selected from the group consisting of creatine kinase, myoglobins, natriuretic proteins, cardiac troponins, CRP, circulatory regulating prohormones, and fragments thereof, respectively.

9. The in vitro method according to claim 6, wherein the ischemic biomarker is one or more biomarkers selected form the group consisting of troponin-I, troponin-T and CK-MB.

10. The in vitro method according to claim 6, wherein the neurohormonal biomarker is one or more biomarkers selected from the group consisting of natriuretic proteins and fragments thereof.

11. The in vitro method according to claim 6, wherein the level of said biomarkers is determined in parallel or simultaneously.

12. The in vitro method according to claim 6, wherein the determination of said biomarkers is conducted in one or more samples obtained from said patient.

13. The in vitro method according to claim 1, wherein said determination is conducted by means of an automated analysis device.

14. The in vitro method according to claim 1, wherein said determination is conducted via a rapid test.

15. The in vitro method according to claim 1, wherein the determination is conducted for risk stratification in said patient.

16. The in vitro method according to claim 1, wherein the diagnosis is conducted for risk stratification in said patient for making clinically relevant decisions concerning further treatment options, by means of pharmaceuticals for the use in the treatment or therapy or cardiac insufficiency, and treatment of infections and/or inflammatory diseases of the respiratory tract and lung, as well as for the control of administering antibiotics, or intensive care or emergency medicine treatment.

17. The in vitro method according to claim 1, wherein the diagnosis is conducted for prophylaxis, for early differential diagnosis or diagnosis, for assessment of the degree of severity, or for therapy-accompanied-evaluation of follow-up on infections or inflammatory diseases of the respiratory tract and lung with associated cardiac insufficiency in said patient.

18. The in vitro method according to claim 1, wherein the infection is caused by bronchitis, pneumonia, sarcoidosis, bronchiectasis or non-cardiological pulmonary edema.

* * * * *